(12) United States Patent
Noyer et al.

(10) Patent No.: US 11,951,011 B2
(45) Date of Patent: Apr. 9, 2024

(54) LINE OF DUAL MOBILITY JOINT IMPLANT SYSTEMS

(71) Applicant: GILES, Caluire-et-Cuire (FR)

(72) Inventors: Daniel Noyer, Luzinay (FR); Philippe Bauchu, Lyons (FR); Alain Cypres, Saint-Nizier-sous-Charlieu (FR); Arnaud Fiquet, Caluire-et-Cuire (FR); Christophe Roy, Chatuzange-le-Goubet (FR); Olivier Bonnard, Meyzieu (FR); Philippe Girardin, Lezigneux (FR); Bertrand Seutin, La Batie-Rolland (FR); Gualter Vaz, Lyons (FR); Philip John Roberts, Cheshire (GB)

(73) Assignee: GILES, Caluire-et-Cuire (FR)

( * ) Notice: Subject to any disclaimer, the term of this patent is extended or adjusted under 35 U.S.C. 154(b) by 287 days.

(21) Appl. No.: 16/509,985

(22) Filed: Jul. 12, 2019

(65) Prior Publication Data

US 2020/0276021 A1    Sep. 3, 2020

(30) Foreign Application Priority Data

Mar. 1, 2019  (FR) ...................................... 1902133

(51) Int. Cl.
  *A61F 2/34*   (2006.01)
  *A61F 2/30*   (2006.01)
  *A61F 2/36*   (2006.01)

(52) U.S. Cl.
  CPC ............ *A61F 2/34* (2013.01); *A61F 2/30767* (2013.01); *A61F 2/3609* (2013.01);
  (Continued)

(58) Field of Classification Search
  CPC ................ A61F 2/34; A61F 2002/3208; A61F 2002/30665; A61F 2002/30663;
  (Continued)

(56) References Cited

U.S. PATENT DOCUMENTS

| 4,662,891 A | * | 5/1987 | Noiles ....................... A61F 2/34 623/22.31 |
| 4,801,301 A | | 1/1989 | Noiles |

(Continued)

FOREIGN PATENT DOCUMENTS

| EP | 2374432 A1 | 10/2011 |
| FR | 2710836 A1 | 4/1995 |

(Continued)

OTHER PUBLICATIONS

International Search Report and Written Opinion, corresponding International Patent Application No. PCT/FR2020/050297 dated May 7, 2020.

*Primary Examiner* — Brian A Dukert
*Assistant Examiner* — Melissa A Hoban
(74) *Attorney, Agent, or Firm* — MARSHALL, GERSTEIN & BORUN LLP

(57) ABSTRACT

A line of joint implant systems includes an implant including a cup to be affixed in one of the elements of the considered joint, defining a smooth inner cavity of substantially hemispherical shape. The implant also includes an insert, mobile within the inner cavity of the fixation cup and having its smooth outer surface intended to cooperate by ball-and-socket joint with the inner cavity, and defining in turn a smooth inner cavity of substantially hemispherical shape. The implant further includes a head or ball, solid with a second element of the joint, of spherical shape, intended to be received in the inner cavity of the mobile insert and to form a second ball-and-socket joint. The ratio of the inner diameter of the inner cavity of the fixation cup to the inner diameter of the inner cavity of the mobile insert is constant, whatever the diameter of the selected ball.

6 Claims, 2 Drawing Sheets

(52) U.S. Cl.
CPC ............... *A61F 2002/30616* (2013.01); *A61F 2002/3611* (2013.01); *A61F 2220/0033* (2013.01); *A61F 2250/006* (2013.01); *A61F 2310/00059* (2013.01)

(58) Field of Classification Search
CPC ................ A61F 2/30767; A61F 2/3609; A61F 2002/30616; A61F 2002/3611; A61F 2220/0033; A61F 2250/006; A61F 2310/00059; A61F 2/32
See application file for complete search history.

(56) References Cited

U.S. PATENT DOCUMENTS

| | | | | |
|---|---|---|---|---|
| 5,263,988 | A * | 11/1993 | Huebner | A61F 2/32 623/22.29 |
| 5,314,491 | A * | 5/1994 | Thongpreda | A61F 2/32 623/22.29 |
| 7,776,097 | B2 * | 8/2010 | Tepic | A61F 2/30907 623/22.24 |
| 7,833,276 | B2 * | 11/2010 | Auxepaules | A61F 2/32 623/22.18 |
| 8,123,815 | B2 * | 2/2012 | Meridew | A61F 2/34 623/22.29 |
| 9,044,323 | B2 * | 6/2015 | Kyomoto | A61F 2/30767 |
| 9,180,012 | B2 * | 11/2015 | Jordan | A61F 2/4425 |
| 9,445,905 | B2 * | 9/2016 | Muratoglu | A61F 2/468 |
| 9,649,194 | B2 * | 5/2017 | Forsell | A61F 2/3609 |
| 9,820,853 | B2 * | 11/2017 | Meridew | A61F 2/32 |
| 9,999,513 | B2 * | 6/2018 | Overes | A61F 2/40 |
| 2007/0255418 | A1 * | 11/2007 | Bonnard | A61F 2/4225 623/18.11 |
| 2014/0303743 | A1 * | 10/2014 | Choudhury | A61F 2/32 623/22.24 |

FOREIGN PATENT DOCUMENTS

| | | |
|---|---|---|
| WO | WO-2004/069091 A2 | 8/2004 |
| WO | WO-2018/075478 A1 | 4/2018 |

* cited by examiner

LINE OF DUAL MOBILITY JOINT IMPLANT SYSTEMS

TECHNOLOGICAL FIELD

The present disclosure concerns the field of joint implants, particularly dual mobility joint implants, aiming at replacing bone joints of substantially hemispherical geometry of the human or animal body.

It more specifically concerns, without this being a limitation, the hip joint.

BACKGROUND

In the field of total hip prostheses, the so-called principle of dual mobility, that is, of the rotation of a spherical head or ball, affixed to a prosthetic stem inserted into the femur inside of a mobile insert, captured by the sinking fitting said mobile insert, which articulation is generally described as being the small articulation, the mobile insert being most often made of high-density polyethylene, has been known for many years. Said insert is itself also capable of rotating in a cup or an acetabulum anchored in the acetabular cavity of the pelvis, generally called large articulation. The two, small and large, articulations, are called dual mobility. The small articulation is involved in motions of small amplitude and the large articulation starts being actuated when the femoral neck of the prosthetic stem comes into contact with said sinking of the mobile insert in motions of large amplitude. Such a contact is described in literature as being the third articulation, and often the most fragile.

Dual mobility has enabled to significantly decrease dislocations of such a prosthetic joint. Such a prosthesis has for example been described in document FR 2 710 836.

If, undoubtedly, the implementation of such dual mobility hip prostheses has, on the one hand, decreased the number of dislocations of such prosthetic joints and, on the other hand, increased their lifetime, experience shows that there however remain a number of cases for which such dislocation phenomena still appear, or also that jammings of the mobile insert, by multiple factors, within the fixation cup, resulting from the cooperation between the different surfaces of cooperation between the elements forming such prostheses, cause a failure of the prosthesis.

In practice, the orthopedic surgeon facing the need to install a total hip prosthesis can use a range of implants, typically formed of:

a series of fixation cups, having their external diameter discretely and incrementally varying in order to adapt to the different acetabula, having a standard thickness generally in the range from 2 to 4 millimeters;

two or three joint ball or head sizes, generally with a 22- and 28-millimeter diameter, intended, as already mentioned, to be affixed to the prosthetic stem inserted into the femur;

eventually, a series of mobile inserts, taking into account the outer diameter of the ball and the variation of the inner diameter of the inner cavity of the fixation cup.

In other words, in such a range, the surgeon first has to select the adequate mobile insert, taking into account the selected fixation cup as well as the diameter of the selected ball. From a purely physical point of view, it can be observed that the more the diameter of the respective surfaces in contact increases, the more the friction torque increases. Thereby, more wearing is generated at the level of the large articulation, that is, between the mobile insert and the inner cavity of the fixation cup, than at the level of the small articulation, that is, between the head or ball and the inner cavity of the mobile insert, over equivalent motion amplitudes. Thereby, despite the improved quality of the materials used, wear debris is generated, which may cause osteolyses likely to result in a failure of the prosthesis.

Another issue is inherent to the thickness of the mobile insert. Indeed, if the thickness is too small, the ball or head which receives it is capable of cause the breaking of the insert due to the stress received by the latter, typically by creeping, for example. As a corollary, too high a thickness is penalizing at the level of the large articulation, that is, of the cooperation between the outer surface of the insert and the inner cavity of the fixation cup. Indeed, the larger the outer diameter of the insert, the higher its starting torque, related to the friction torque of the involved surfaces and to the mass of the mobile insert, which results in a contact of higher energy at the level of the sinking of the mobile insert, which may be prejudicial in the long term and can often be observed.

Finally, cases of jamming of the large articulation, particularly by fibroses or periprosthetic osteophytes, have also been observed.

The object of the presently described embodiments is to provide a line or range of joint implant systems enable to significantly overcome these different disadvantages.

SUMMARY OF THE DISCLOSURE

For this purpose, the described embodiments aim at a line of joint implant systems, said implant being of the type comprising:

a cup to be affixed in one of the elements of the considered joint, defining a smooth inner cavity of substantially hemispherical shape;

an insert, mobile within the inner cavity of the fixation cup and having its smooth outer surface intended to cooperate by ball-and-socket joint with the inner cavity of the fixation cup, and defining in turn a smooth inner cavity of substantially hemispherical shape;

a head or ball, solid with a second element of the joint, of spherical shape, intended to be received in the inner cavity of the mobile insert and to form a second ball-and-socket joint.

The ratio of the inner diameter of the inner cavity of the fixation cup to the inner diameter of the inner cavity of the mobile insert, for all the elements in the line, is constant.

In other words, the surface area ratio of the small articulation and of the large articulation is constant for a selected ball diameter. Indeed, the respective diameters and surfaces are interconnected by the well known conventional relations of calculation of a sphere, particularly truncated, concerning the insert.

Thereby, whatever the selected parameter (diameter or surface area), the constant character of the respective ratio is maintained.

In other words, the surgeon determines, after the milling of the patient's acetabulum, the outer diameter of the appropriate fixation cup, in particular to keep as much bone stock as possible. The determined fixation cup will have a thickness such that it respects the previously-mentioned constant size ratio, to decrease the friction torque of the large articulation and, as a corollary, to further decrease dislocation phenomena, in addition to the wear phenomena capable of causing, as previously indicated, the jamming of the joint and other above-mentioned risks of prosthetic failure.

Advantageously, the ratio is in the range from 1.1 to 3.

BRIEF DESCRIPTION OF THE DRAWINGS

The foregoing and other features and advantages of the present embodiments will be discussed in detail in the following non-limiting description, in connection with the accompanying drawings, in which.

DETAILED DESCRIPTION

Figure 1:
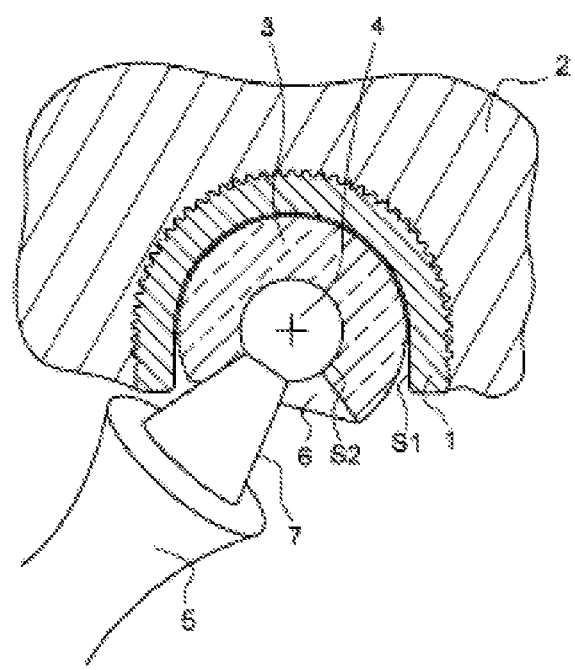
FIG. 1 is a simplified representation illustrating a dual mobility joint implant according to prior art.

As already indicated, FIG. 1 shows the schematic diagram of a dual mobility joint implant according to the prior state of the art.

Basically, the implant is first formed of a cap-shaped fixation cup (1) intended to be affixed within a first element of a joint to be fitted with a prosthesis (2), and for example, the acetabular cavity of a patient's pelvis in the context of a hip prosthesis.

The fixation cup is made of a biocompatible rigid material, and for example made of metal such as one-piece chromium-cobalt, or a chromium-cobalt composite with a trabecular titanium additional thickness, for example, in order to lighten it. The fixation cup defines an inner cavity having a substantially hemispherical shape, defining a first inner articulation surface (S1).

The inner cavity of the fixation cup is intended to receive and to cooperate with a mobile insert (3), also made of biocompatible material, and typically made of high-density polyethylene. The mobile insert (3), also having a substantially hemispherical shape, is thus intended to be received in the inner cavity of the fixation cup (1) to form a first ball-and-socket joint called large articulation. The outer diameter of the mobile insert (3) is thus, to within the clearance, substantially equal to the inner diameter of the inner cavity of the fixation cup (1).

The mobile insert (3) also comprises an inner cavity, also having a substantially hemispherical shape, and defining a second articulation surface (S2), called small articulation, said inner cavity being intended to receive and to cooperate with a spherical head or ball (4), solid with another element of the prosthesized joint, in the case in point, with a femoral stem (5), inserted into the medullary cavity of the femur of the considered joint.

Conventionally, the ball (4) is mounted on a Morse taper located at the end of the neck (7) of the femoral stem (5), and this, in known fashion. The femoral stem is typically made of a biocompatible rigid material such as titanium, chromium-cobalt, stainless steel, etc.

Thereby, a possible double rotating motion according to a double ball-and-socket joint, respectively of the mobile insert (3) with respect to the fixation cup (1) and of the ball (4) with respect to the mobile insert (3) is created.

Advantageously, and to optimize the range of motion of the joint, and accordingly to limit dislocation phenomena, the base of the mobile insert has a flared shape defining a sinking (6), capable of cooperating with the tapered shape of the neck (7) located at the upper end of the stem (5).

In known fashion, the dimensions of the fixation cup (1) are inherent, on the one hand, to the considered joint, with as a main object the conservation of the patient's bone stock, and on the other hand, to the stress that it is intended to withstand. Conventionally, concerning a hip joint implant, the outer diameter of the fixation cups of a line typically varies between 44 and 74 millimeters with a 2-millimeter increment.

The thickness of the fixation cup of prior art implants is constant in a standard line, and thus according to the growth of the outer diameter thereof, the articulation surface (S1), that is, the inner surface area of the inner cavity of the fixation cup, as well as the thickness of the mobile insert, are impacted according to this growth. Due to the increase in the insert thickness, the articulation surface area (S1) increases, and thus, accordingly, the friction torque at this level increases. As a result, the wear of the prosthesis at this level also increases for motions of large amplitude.

Similarly, two sizes of joint balls (4) are conventionally retained, for a hip prosthesis, respectively with a diameter of 22 and of 28 mm.

It can be inferred that, as previously indicated, with prior art implants, to take into account the variation of the diameter of the fixation cup (1) and the standard diameter of the ball (4), the size of the mobile insert will vary, and more particularly its outer diameter, in contact with articulation surface S1, thereby increasing its thickness.

Once the outer diameter of the fixation cup has been determined by the surgeon, according to the state of the patient's acetabulum after milling and to the desired maximum conservation of the bone stock, within a same line of such joint implants, the selection of the insert and accordingly that of the ball can be naturally deduced. More practically, for outer diameters of fixation cups typically in the range from 52 to 74 millimeters, a ball having a 28-millimeter diameter will be preferred to limit the friction torque at the level of surface S1. Once the ball has been selected, there is no further choice concerning the insert, there being only one insert for a ball of determined diameter. However, and given this uniqueness, the selection of the fixation cup in terms of thickness is dictated by the constant ratio desired by the embodiments of the inner diameter of the inner cavity of the fixation cup, in the case in point, of the surface of the joint (S1), to the inner diameter of the mobile implant, and thus, in the case in point, (S2), and typically in the range from 1.1 to 3, advantageously close to 1.6.

However, for outer diameters of fixation cups smaller than 52 millimeters, a ball having a 22-millimeter diameter will be favored, thus determining the selection of the second insert in the line of implants, having an inner cavity adapted to such a ball diameter. Here again, the selection of the fixation cup in terms of thickness is directly inherent to this insert, still to respect to constant ratio of the embodiments.

In the described example of hip prosthesis implants, and, the considered line or range only comprises two balls, respectively having a 22- or 28-millimeter diameter, and as a corollary two mobile inserts, depending on the selected ball diameter.

In other words, taking into account, on the one hand, the selected mobile insert (itself only depending on the diameter of the selected ball) and, on the other hand, the outer diameter of the fixation cup, determined by the acetabular environment observed by the surgeon, the surgeon is capable of selecting the fixation cup best adapted for the desired result while respecting the ratio.

Figure 2:
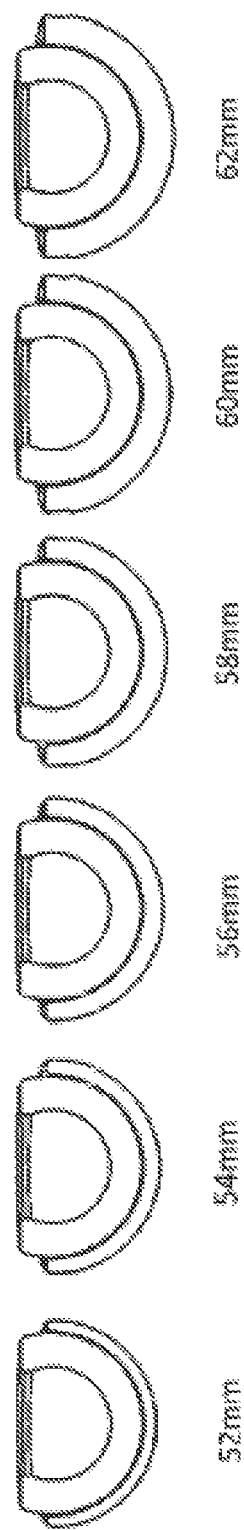
FIG. 2 is a series of sagittal sections of a line or range of joint implants, mainly illustrating the variation of the thickness, in particular, of the outer cup.

In the case in point, FIG. 2 shows a series of sagittal section views of different cups/mobile insert pairs, where it can be observed that for a given mobile insert, here adapted for a ball having a 28-millimeter diameter, the thickness of the fixation cup increase with the increase of its outer diameter, to respect the constant character of the ratio of the diameters, respectively the inner diameter of the fixation cup and the inner diameter of the insert. In other words, if the range of balls (4) comprises two sizes, typically having a 22-millimeter diameter and a 28-millimeter diameter for a hip, there are for the line of inserts (3) only two sizes respectively corresponding to the sizes of the balls (4). Practically, one can see in FIG. 2, from left to right, six fixation cups having an outer diameter varying from 52 to 62 millimeters, with a discrete 2-millimeter increment, and accordingly a single mobile insert, adapted for a 28-millimeter ball.

The situation is strictly the same for fixation cups having an outer diameter varying from 44 to 50 millimeters, with the difference that the ball diameter is here 22 millimeters, and that accordingly, the used insert is adapted to such a ball diameter.

With the compliance with such a ratio, the present embodiments aim at further significantly decreasing the few prosthetic failures of prior art dual mobility implants. Indeed, the decrease in the starting torque difference in the joint between the small and the large articulation results in:
- on the one hand, the fact that when the prosthetic neck of the stem comes into contact with the mobile insert in large ranges of motion, the large articulation requires less energy to be actuated and thus results being less damaging for the sinking of the mobile insert, which is the weak point of dual mobility implants, and
- on the other hand, the external surface area of the mobile insert is optimized so that, even in fixation cups having a large outer diameter, the outer surface area of said mobile insert remains constant and limited, thus limiting wear debris capable of causing osteolyses and, thus, prosthetic failures; literature shows that the number of particles emitted in a hip joint is a function, among others, of said outer surface area of the mobile insert.

Accordingly, due to the decrease in the friction torque, wear phenomena, which inevitably appear despite the use of high-hardness materials, are also decreased, thus causing a debris decrease, and thus optimizing the lifetime of such joint implants.

The advantages of the presently described embodiments which, in addition to decreasing dislocation phenomena, on the one hand, and debris genesis, on the other hand, enable in economical terms to decrease the number of elements belonging to a line of joint implants, and in logistic terms, to decrease stocks, thus become apparent.

Further, in terms of patient security, the simplification of the number of joint implants avoids a number of operation errors, such as resulting from labeling errors or errors of size compatibility between the mobile insert and the fixation cup.

The invention claimed is:

1. A set of components for creating joint implant systems, the set of components including balls having a plurality of different diameters, a plurality of mobile inserts each corresponding to one of the balls, and a plurality of cups, each joint implant system comprising:
   a cup configured to be affixed in an element of a considered joint, defining a first smooth inner cavity of substantially hemispherical shape, said first cavity having a first inner diameter;
   a mobile insert within the inner cavity of the cup and having a smooth outer surface configured to cooperate by a first ball-and-socket joint with the first smooth inner cavity of the cup, and defining second smooth inner cavity of substantially hemispherical shape, said second cavity having a second inner diameter corresponding to one of the plurality of different diameters of the balls;
   a ball of spherical shape having a respective diameter of the plurality of different diameters, said ball being solid with a second element of the considered joint, and being configured to be received in the second smooth inner cavity and to form a second ball-and-socket joint,
   wherein a ratio of the first inner diameter of the first smooth inner cavity to the second inner diameter of the second smooth inner cavity for all of the joint implant systems achievable from the set of components, is constant, regardless of the respective diameter of the ball.

2. The set of components of claim 1, wherein the ratio is in the range from 1.1 to 3.

3. The set of components of claim 1, wherein a thickness of the mobile insert remains constant for a given ball size, regardless of the cup used.

4. The set of components of claim 1, wherein the mobile insert comprises, at a level of a base of the mobile insert, a sinking, configured to cooperate with the second element of the considered joint.

5. The set of components of claim 1, wherein the ratio is 1.6.

6. A set of components for creating joint implant systems, the set of components including balls having a plurality of different diameters, a plurality of mobile inserts each corresponding to one of the balls, and a plurality of cups, each joint implant system comprising:
   a ball, a mobile insert corresponding to a respective diameter of the ball, and one or more cups of the plurality of cups, the one or more plurality of cups configured to be mated with the ball and mobile insert; wherein:
   the one or more cups is configured to be affixed in an element of a considered joint, and defines a first smooth inner cavity of substantially hemispherical shape, said first smooth inner cavity having a first inner diameter;
   the mobile insert is disposed within the first smooth inner cavity of the cup and has a smooth outer surface configured to cooperate by a first ball-and-socket joint with the first smooth inner cavity of the cup, and defines a second smooth inner cavity of substantially hemispherical shape, said second smooth inner cavity having a second inner diameter;
   the ball is of spherical shape having the respective diameter of the plurality of different diameters, said ball being solid with a second element of the considered joint, and being configured to be received in the second smooth inner cavity and to form a second ball-and-socket joint,
   wherein a ratio of the first inner diameter of the first smooth inner cavity to the second inner diameter of the second smooth inner cavity for all of the joint implant systems achievable from the set of components, is constant, regardless of the respective diameter of the ball.

* * * * *